US006772636B2

(12) United States Patent
Lam et al.

(10) Patent No.: US 6,772,636 B2
(45) Date of Patent: Aug. 10, 2004

(54) PIPE FLAW DETECTOR

(75) Inventors: Clive Chemo Lam, Tomball, TX (US); Gregory Michael Vaselakos, Webster, TX (US)

(73) Assignee: Varco I/P, Inc., Houston, TX (US)

( * ) Notice: Subject to any disclaimer, the term of this patent is extended or adjusted under 35 U.S.C. 154(b) by 0 days.

(21) Appl. No.: 10/290,103

(22) Filed: Nov. 6, 2002

(65) Prior Publication Data

US 2004/0083815 A1 May 6, 2004

(51) Int. Cl.[7] ............................ G01N 29/24; G01N 29/26
(52) U.S. Cl. .............................. 73/622; 73/638; 73/639
(58) Field of Search ........................... 73/620, 622–625, 73/627–629, 632–634, 639, 637, 638

(56) References Cited

U.S. PATENT DOCUMENTS

| 3,741,003 | A |   | 6/1973  | Gunkel ............... 73/67.7 |
| 4,012,946 | A |   | 3/1977  | Patsey ............... 73/67.7 |
| 4,289,033 | A | * | 9/1981  | Prause et al. ....... 73/622 |
| 4,524,622 | A | * | 6/1985  | Suzuki et al. ....... 73/620 |
| 4,700,572 | A |   | 10/1987 | Senba et al. ....... 73/622 |
| 4,870,866 | A |   | 10/1989 | Slack ............... 73/599 |
| 5,007,291 | A |   | 4/1991  | Walters et al. ...... 73/640 |
| 5,402,682 | A | * | 4/1995  | Patzke ............... 73/622 |
| 5,447,070 | A | * | 9/1995  | Patzke et al. ....... 73/621 |
| 5,485,751 | A | * | 1/1996  | Karbach et al. ...... 73/618 |
| 5,870,669 | A |   | 2/1999  | Kawai ............... 435/209 |
| RE36,130  | E |   | 3/1999  | Haynes .............. 73/622 |
| 5,907,491 | A |   | 5/1999  | Canada et al. ....... 364/468.15 |
| 5,992,236 | A | * | 11/1999 | White et al. ........ 73/622 |
| 6,138,078 | A |   | 10/2000 | Canada et al. ....... 702/44 |
| 6,216,539 | B1|   | 4/2001  | Johnson et al. ...... 73/592 |
| 6,220,098 | B1|   | 4/2001  | Johnson et al. ...... 73/592 |
| 6,247,353 | B1|   | 6/2001  | Battenberg et al. ... 73/40.5 |

OTHER PUBLICATIONS

Ultrasonic NDT Instruments and Systems, Matec Instruments Companies, 2001.
Truweld Ultrasonic Weld Line Inspection System, Tuboscope, Inc., 2001.

* cited by examiner

*Primary Examiner*—Hezron Williams
*Assistant Examiner*—Rose M. Miller
(74) *Attorney, Agent, or Firm*—Guy McClung

(57) ABSTRACT

A detector for detecting a location of a flaw on a tubular member, the tubular member having a longitudinal axis, the detector having a body, dial rotatably mounted to the body, the dial with directions indications thereon for indicating position of the dial with respect to the longitudinal axis of the tubular member, and ultrasonic probe apparatus secured to the dial for selective positioning by rotating the dial for facilitating location of a flaw of the tubular member; and, in certain aspects, detectors for measuring tubular wall thickness.

17 Claims, 4 Drawing Sheets

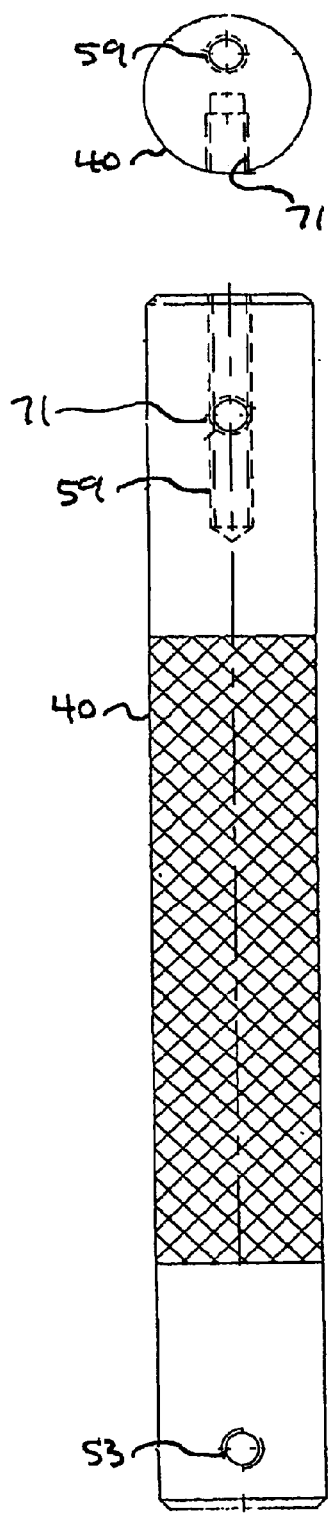
Fig. 5A
Fig. 5B
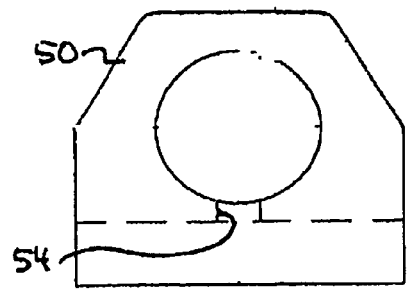
Fig. 6A
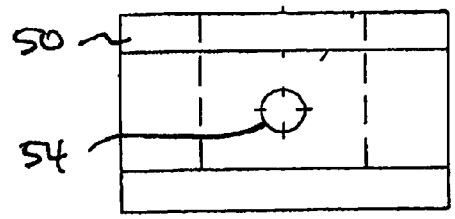
Fig. 6B
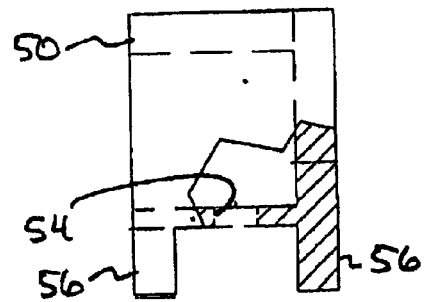
Fig. 6C
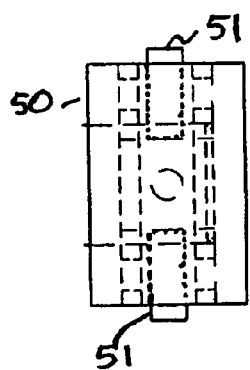
Fig. 6D

PIPE FLAW DETECTOR

BACKGROUND OF THE INVENTION

1. Field of the Invention

The present invention is directed to pipe flaw detectors and, in one particular aspect, to a manually operable defect locator.

2. Description of Related Art

The prior art discloses a variety of systems for inspecting pipe and tubulars which are used to detect and locate both inner diameter and outer diameter flaws and defects. These systems provide a fairly accurate flaw location on the pipe and, in the case of an "oblique" flaw, a measurement of an angle of the flaw with respect to the longitudinal axis of the pipe or tubular. Following this detection and location of the flaw, personnel visually locate the flaw so that an attempt may be made to grind the flaw away or grind it to such an extent that the pipe wall thickness at that location is within certain acceptable limits.

In the past systems and apparatuses for the post-inspection location of a flaw have included a hand-held ultrasonic probe. Certain of these prior art apparatuses and systems provide inaccurate flaw locations and do not adequately deal with differences in tubulars' outer curvature.

There has long been a need, recognized by the present inventors, for an easily manipulable device or apparatus for post-machine-inspection flaw location. There has long been a need for such a device or apparatus which provides an accurate location of a flaw.

SUMMARY OF THE PRESENT INVENTION

The present invention, in certain embodiments, discloses a post-machine-inspection pipe flaw detector that provides an operator a precise determination of flaw location. In one aspect, such a detector is a hand-held manually manipulable device with a search head with one or more ultrasonic probes that is movable over a pipe or other tubular. By setting an adjustable direction device, such a detector can be used to detect transverse, longitudinal and oblique flaws. The ultrasonic probe (or probes) is connected to a typical ultrasonic probe system with instrumentation, receiver(s), processor (s), display(s), etc., as are well known in the art and are commercially available. A coupling device, preferably with a flexible member for conforming to a tubular's curvature, (e.g., but not limited to, a water-filled bladder and a flexible ultrasonic wave guide) is positioned beneath the ultrasonic probe(s) for contacting the pipe with the flaw (or flaws) to be located. An operator, who has information generated by a previous machine inspection of the pipe and knows the general flaw location and orientation, places the detector in the known area of the flaw moving the detector around, if necessary, to precisely locate the flaw.

The search head of the detector has a movable dial member with angular marking indicators from 0° to 180° which correspond to possible angular measurements of the angle of a flaw's orientation (previously determined by the machine inspection) with respect to the longitudinal axis of the pipe. The operator sets the dial member's angular indicator to the previously-measured angle of the flaw determined by the previous inspection, and this moves the ultrasonic probe position on the dial member so that its angular orientation with respect to the pipe's longitudinal axis corresponds to the angular setting of the dial member and thus to the angle of the flaw with respect to the pipe's longitudinal axis.

This facilitates the location of the flaw and indicates that a detected flaw is the flaw indicated by the previous machine inspection.

Once the operator has located the flaw it is possible to grind, sand, or otherwise abrade the flaw in an effort to bring the pipe wall thickness at the flaw location into acceptable tolerances, e.g. in one particular aspect, within 5%, plus or minus, of the average acceptable wall thickness. Such grinding can reduce stress at the location of a flaw.

In certain embodiments one or more rollers are provided at the lower surface of the search head to facilitate the movement of the search head over a pipe's outer surface. In certain aspects a handle is connected to the head for holding the head and, optionally, such a handle may have one or more rollers on its lower surface for contacting the pipe's outer surface. Alternatively, the search head may have an upper handle with or without roller(s) to facilitate its movement and handling by an operator.

In one aspect connections are provided on the search head for introducing and evacuating a coupling fluid, e.g. water, to the bladder positioned beneath the ultrasonic probe(s) and/or for evacuating air from the bladder. These connections may extend through the dial member or through any other suitable part of the search head or handle (if one is present).

optionally, one or more additional ultrasonic wall thickness probes may be mounted on the search head [e.g., on the dial, body or handle]. In certain aspects, apparatus according to the present invention is used for primary flaw detection—i.e., a previous inspection by machine is not done.

It is, therefore, an object of at least certain preferred embodiments of the present invention to provide:

New, useful, unique, efficient, non-obvious devices for post-machine-inspection location of pipe or tubular flaws and defects;

Such devices which accurately locate longitudinal, transverse, and oblique flaws;

Such devices which are easily manipulable and easily handled by an operator;

Such devices which in one aspect have one or more rollers to facilitate movement over a pipe or tubular's surface and, in certain aspects, facilitate proper alignment of the device with respect to a tubular and/or with respect to a flaw; and which, in one particular aspect, have at least two spaced-apart pairs of rollers to span portions of a tubular's curved surface to correctly position a device according to the present invention with respect to a longitudinal axis of the tubular;

Such devices with one or more roller apparatuses to maintain a desired distance between an ultrasonic transducer and a tubular surface and/or flaw;

Such devices which can detect and distinguish between inner diameter and outer diameter flaws;

Such devices with angular indicators to correctly align an ultrasonic probe on the device with a flaw that is at an angle to the pipe axis to facilitate detection of such a flaw;

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of certain embodiments of the invention may be had by references to the embodiments which are shown in the drawings which form a part of this specification.

FIG. 5A is an end view and FIG. 5B is a side view of a handle of the flaw detector of FIG. 1A.

FIG. 6A is a top view, FIG. 6B is a bottom view and FIG. 6C is a side view of part of the flaw detector of FIG. 1A. FIG. 6D is a top view of a roller apparatus of the device of FIG. 1A.

DESCRIPTION OF EMBODIMENTS PREFERRED AT THE TIME OF FILING FOR THIS PATENT

Figure 1A:
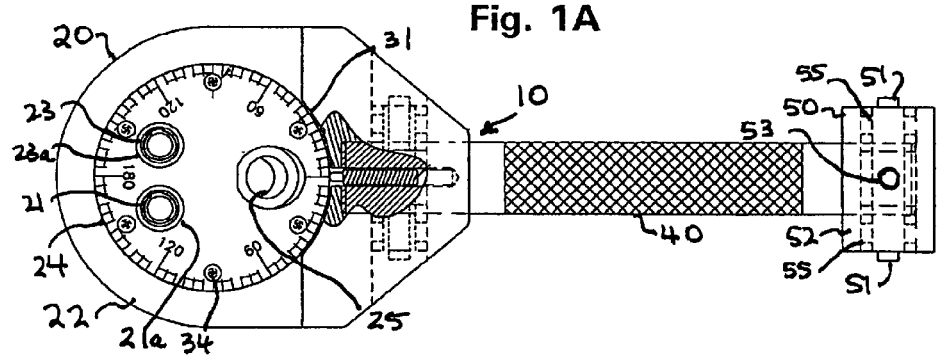
FIG. 1A is a top view of a flaw detector according to the present invention.
Figure 1B:
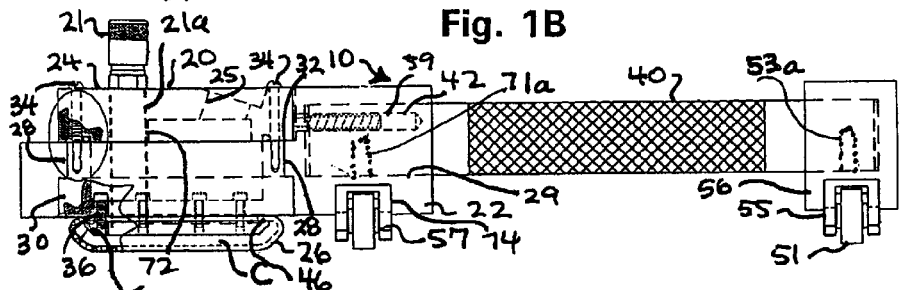
FIG. 1B is a side view, partially in cross-section, of the flaw detector of FIG. 1A.
Figure 1C:
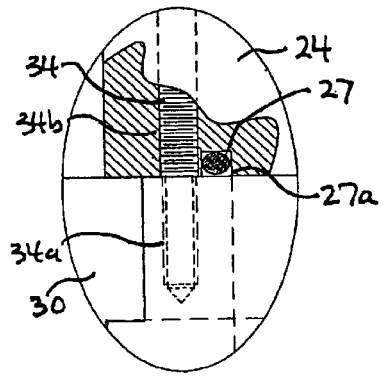
FIG. 1C is an enlarged view of part of the flaw detector of FIG. 1A.
Figure 2A:
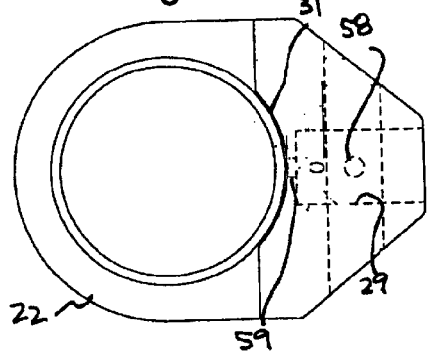
FIG. 2A is a top view of part of the flaw detector of FIG. 1A.
Figure 2B:
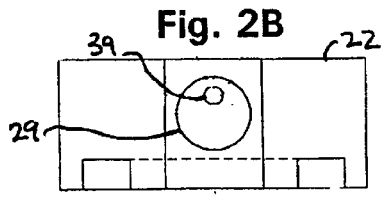
FIG. 2B is an end view and FIG. 2C is a side view of the part of FIG. 2A.
Figure 2C:
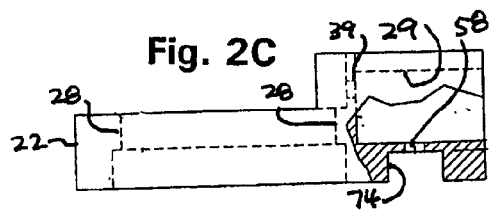
Figure 3A:
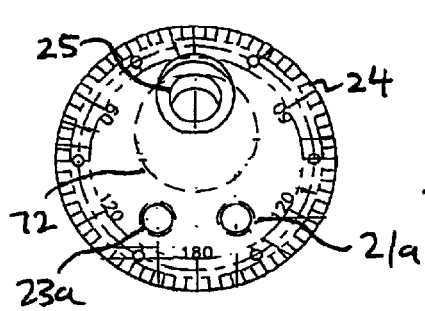
FIG. 3A is a top view of a dial member of the flaw detector of FIG. 1A.
Figure 3B:
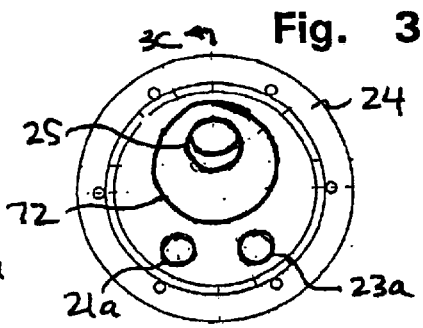
FIG. 3B is a bottom view of the dial member of FIG. 3A.
Figure 3C:
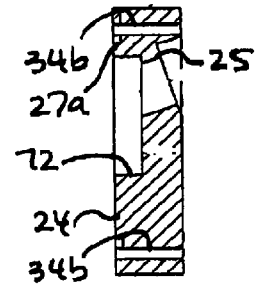
FIG. 3C is a view along line 3C—3C of FIG. 3B.

FIGS. 1A and 1B show a device 10 according to the present invention for pipe and tubular flaw and defect detection which has a search head 20 and a handle 40. The search head 20 has a body 22 to which is movably and rotatably mounted a dial member 24 and optional bladder 26. A lip 46 of the bladder 26 is secured with a tight press fit over a ring 45 which extends around screws 36 in a mount member 30 which itself is secured to the dial member 24 with screws 24a. An o-ring 47 in a groove 48 seals a bladder-26/mount member-30 interface.

Projections 28 of the body 22 project into a recess 32 defined by part of the lower surface of the dial member 24, an outer surface of the mount member 30, and part of the upper surface of the mount member 30.

A roller apparatus 50 with two spaced-apart rotatable rollers 51 is mounted to a mount member 52 which itself is secured to the handle 40. A screw 53 through a hole 54 secures the mount member 50 to the handle 40. Roller mounts 55 are positioned between legs 5 of the mount member 50. A roller apparatus 57, like the roller apparatus that includes the roller 51, is mounted in a recess 74 on the bottom of the body 22 and secured in place with a screw through a hole 58. A screw 42 through holes 39 and 59 secures the handle 40 to the body 22 with an end of the handle 40 projecting into a recess 29 of the body 22. By selecting a desired diameter for the rollers and their mounting locations, a desired distance may be maintained between ultrasonic transducer(s) on the apparatus and a tubular surface.

Connections 21 and 23 and holes 21a and 23a, respectively, provide passages for the introduction of coupling fluid into the bladder 26 and for the evacuation of fluid (and air, if present) from the bladder 26. An opening 25 is sized and configured for holding an ultrasonic probe, e.g., but not limited to as described in U.S. Pat. Nos. 5,914,596; 5,313,837; 5,00,069; and 5,656,786; and in pending U.S. applications Ser. Nos. 09/930,117 filed 14 Aug. 2001 and Ser. No. 10/052,237 filed 18 Jan. 2002—all said patents and applications incorporated fully herein for all purposes. An o-ring 27 surrounds the dial member 24 and seals an interface between the dial member 24 and the mount member 30. Coupling fluid C is located inside the body 22 and above the bladder 26.

Part of the dial member 24 fits into a recess 31 of the body 22. Fasteners 53a and 71a are used in holes 53 and 71, respectively, to connect parts 22 and 50 to the handle 40.

Figure 4A:
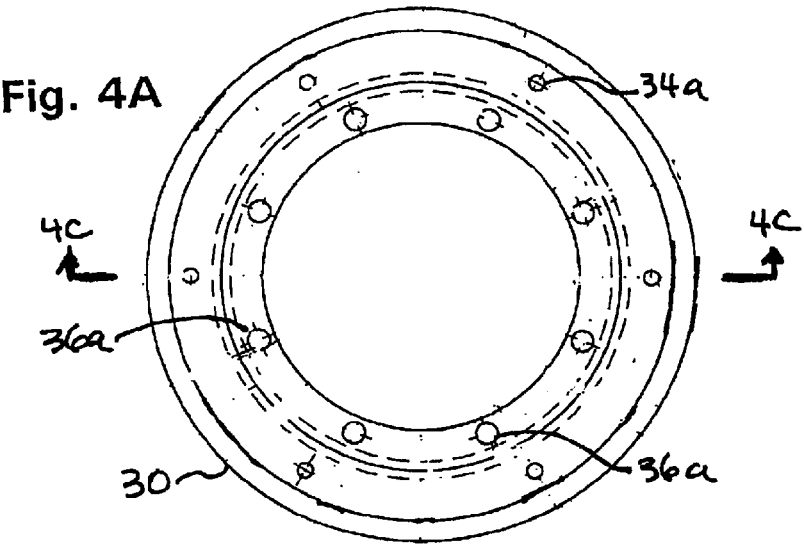
FIG. 4A is a top view of part of the flaw detector of FIG. 1A.
Figure 4B:
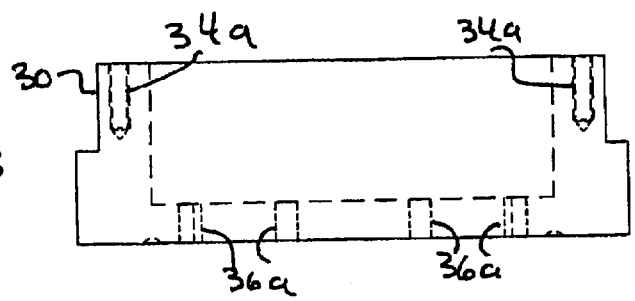
FIG. 4B is a side view of the part of FIG. 4A.
Figure 4C:
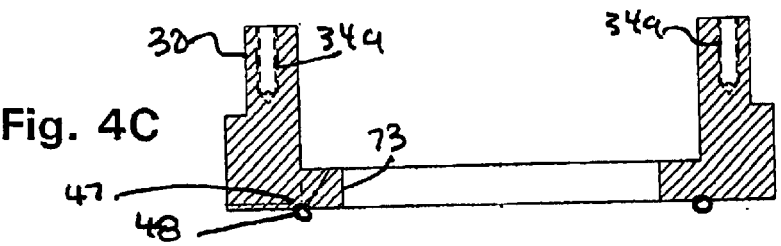
FIG. 4C is a view along line 4C—4C of FIG. 4A.

The mount member 30 as shown in FIGS. 4A–4C has holes 34a for the screws 34 and holes 36a for the screws 36. The dial member 24 has holes 34b for the screws 34 and a recess 27a for the ring 27. Ultrasonic sound from the ultrasonic transducer passes through the opening 73 through coupling fluid C and out from the bladder 26.

Figure 7:
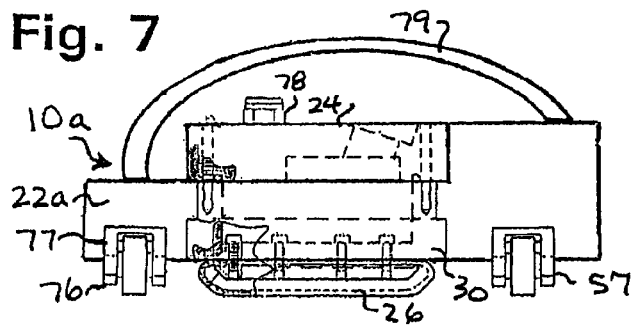
FIG. 7 is a side view of a flaw detector according to the present invention.

FIG. 7 shows a flaw detector 10a similar to the flaw detector 10, FIG. 1A; but without a handle 40 and with an additional roller apparatus 76 in a recess 77 in a body 22a (which is similar to the body 22, FIG. 1A). A handle 79 for holding the flaw detector 10a is secured to the body 22a. Alternatively, the roller apparatus 57 may be deleted and/or the roller apparatus 76 may be deleted (as may be any roller apparatus from any detector according to the present invention).

Figure 8A:
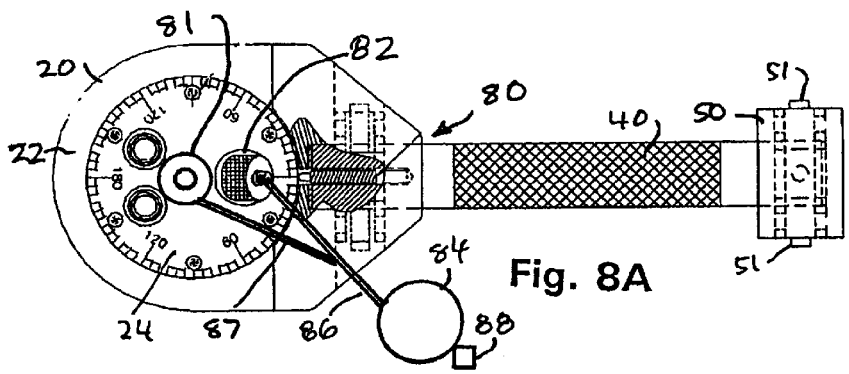
FIG. 8A is a top view of a flaw detector according to the present invention.
Figure 8B:
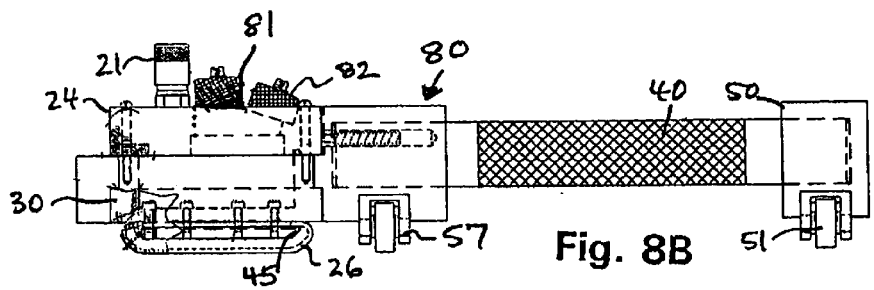
FIG. 8B is a side view, partially in cross-section, of the flaw detector of FIG. 8A.

FIGS. 8A and 8B show a flaw detector 80 according to the present invention which is like the flaw detector 10, FIG. 1A (and like numerals indicate like parts). The flaw detector 80 has ultrasonic probe apparatus 82 which is in communication with and connected to signal/data reception/processing apparatus 84 via wire(s), conduits, etc. 86. Any detector according to the present invention may be thus connected to and in communication with an apparatus 84 (shown schematically) or similar apparatus. As an operator positions the flaw detector 80 on pipe or tubulars for locating a flaw, and, if necessary, moves the detector, a display, screen, chart, or other output 88 indicates that the flaw being sought has been found. (Items 84, 86 and 88 are shown only in FIG. 8A.) Then the operator can remove the detector, visually locate the flaw, and, if deemed appropriate, grind, sand, or otherwise abrade the flaw in an effort to bring the wall thickness at that location within acceptable tolerances.

As shown in FIGS. 8A and 8B, the detector 80, optionally (as may be the case for any detector according to the present invention) has a wall thickness ultrasonic probe apparatus 81 which may have its own processing apparatus, or which may, as shown, be in communication via line 87 with the apparatus 84.

Roller apparatuses according to the present invention, in certain aspects include two spaced-apart rollers and at least two such apparatuses are used (e.g., but not limited to, as the roller apparatuses 50 and 57, FIGS. 1A, 1B). As shown in FIG. 6D, these apparatuses have two rollers (e.g. the rollers 51) which are spaced-apart. By thus situating two pairs of spaced-apart rollers on a body or handle of a device according to the present invention, correct alignment of the device with a tubular's curved outer surface is facilitated, i.e., when the device is placed on the tubular so that all four rollers are in contact with the curved tubular surface, the device will be aligned with the tubular's longitudinal axis.

It is within the scope of this invention to substitute for any of the roller apparatuses disclosed herein cushioning and/or resilient and/or solid material to facilitate movement of a flaw detector over the surface of a tubular, including, but not limited to, flat or curved areas or pieces of foam, rubber, plastic, polytetrafluoroethylene, wood, fiberglass, or metal.

Figure 9:
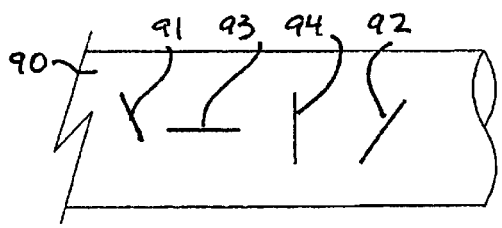
FIG. 9 is a top partial view of a pipe with flaws.

FIG. 9 shows a tubular 90 with two oblique flaws 91 and 92, one in each direction, a longitudinal flaw 93, and a transverse flaw 94. A device according to the present invention may be used to facilitate location of any of these flaws for further processing.

The present invention, therefore, provides in some, but not necessarily all, embodiments, a detector for detecting a location of a flaw on a tubular member (e.g., but not limited to, pipe, casing, tubing, risers), the tubular member having a longitudinal axis, the detector including a body, a dial rotatably mounted to the body, the dial with direction indications thereon for indicating position of the dial with respect to the longitudinal axis of the tubular member, and ultrasonic probe apparatus secured to the dial for selective positioning by rotating the dial for facilitating location of a flaw (e.g. longitudinal flaw, transverse flaw, oblique flaw) of the tubular member. Such a detector may have one or some, in any possible combination of the following: a coupling device mounted to the body beneath the ultrasonic probe apparatus, the coupling device containing coupling fluid; wherein the coupling device rotates with the dial; wherein the tubular member has an outer curved surface and the coupling device includes a flexible member for contacting the outer curved surface of the tubular and for conforming thereto to facilitate operation of the ultrasonic probe apparatus; cushion apparatus and/or roller apparatus on the body, the roller apparatus with at least one rotatable roller for facilitating movement of the body over a surface of the tubular member; wherein the at least one rotatable roller of the roller apparatus is two spaced-apart rollers; wherein the roller apparatus is two spaced-apart pairs of spaced-apart rotatable rollers; wherein the spaced-apart rotatable rollers of each pair of spaced-apart rotatable rollers are sufficiently spaced-apart to align the body with the longitudinal axis of the tubular member when the rotatable rollers are in contact with the tubular member; wherein the direction indications correspond to an angular measurement indicating an angle with respect to the longitudinal axis of the tubular member; wherein the dial can be set to correspond to an angular measurement corresponding to an angle of a flaw with respect to the longitudinal axis of the tubular member; access apparatus for introducing coupling fluid into the coupling device and for evacuating coupling fluid from the coupling device; handle apparatus connected to the body for facilitating handling of the detector; ultrasonic probe apparatus on the detector (e.g. on the body, dial, or handle) for measuring wall thickness of a tubular member; processing apparatus in communication with the ultrasonic probe apparatus for receiving and processing signals from the ultrasonic probe apparatus; and/or wherein the processing apparatus includes display apparatus (e.g., screen and/or print-out and/or strip chart) for displaying processing results.

The present invention, therefore, provides in some, but not necessarily all, embodiments, a detector for detecting a location of a flaw on a tubular member, the tubular member having a longitudinal axis, the detector including a body, a dial rotatably mounted to the body, the dial with direction indications thereon for indicating position of the dial with respect to the longitudinal axis of the tubular member, ultrasonic probe apparatus secured to the dial for selective positioning by rotating the dial for facilitating location of a flaw of the tubular member, a coupling device mounted to the body beneath the ultrasonic probe apparatus, the coupling device containing coupling fluid, wherein the coupling device rotates with the dial, wherein the tubular member has an outer curved surface and the coupling device includes a flexible member for contacting the outer curved surface of the tubular member and for conforming thereto to facilitate operation of the ultrasonic probe apparatus, roller apparatus on the body for facilitating movement of the body over a surface of the tubular member, the roller apparatus comprising two spaced-apart pairs of spaced-apart rotatable rollers, said pairs of spaced-apart rotatable rollers for aligning the body with the longitudinal axis of the tubular member by placing the rotatable rollers in contact with the tubular member, and access apparatus for introducing coupling fluid into the coupling device and for evacuating coupling fluid from the coupling device. Such a detector may have one or some, in any possible combination of the following: ultrasonic probe apparatus on the detector for measuring wall thickness of a tubular member; processing apparatus in communication with the ultrasonic probe apparatus for receiving and processing signals from the ultrasonic probe apparatus; and/or wherein the processing apparatus includes display apparatus for displaying processing results.

The present invention, therefore, provides in some, but not necessarily all, embodiments, a method for detecting a location of a flaw on a tubular member having a longitudinal axis, the method including positioning a detector on an outer surface of the tubular member, the detector as any disclosed herein according to the present invention, rotating a dial of the detector to selectively position ultrasonic probe apparatus of the detector with respect to the longitudinal axis of the tubular member, and locating a flaw with the detector; and, in certain aspects the detector including ultrasonic probe apparatus for measuring a wall thickness of the tubular member, the method further including measuring a wall thickness of the tubular member with the detector.

The present invention, therefore, provides in some, but not necessarily all, embodiments, a device for measuring wall thickness of a wall of a tubular member, the device including a body, ultrasonic probe apparatus secured to the body for providing ultrasonic signals for measuring tubular member wall thickness, a coupling device mounted to the body beneath the ultrasonic probe apparatus, the coupling device containing coupling fluid, and movement facilitation apparatus on the body for facilitating movement of the body over a surface of the tubular member. Such a device may have one or some, in any possible combination, of the following: wherein the tubular member has an outer curved surface and the coupling device includes a flexible member for contacting the outer curved surface of the tubular and for conforming thereto to facilitate operation of the ultrasonic probe apparatus; wherein the movement facilitation apparatus includes roller apparatus which in one aspect has two spaced-apart rotatable rollers, in one aspect has two spaced-apart pairs of spaced-apart rotatable rollers, and in one aspect spaced-apart rotatable roller pairs sufficiently spaced-apart to align the body with the longitudinal axis of the tubular member when the rotatable rollers are in contact with the tubular member; processing apparatus in communication with the ultrasonic probe apparatus for receiving and processing signals from the ultrasonic probe apparatus; and/or wherein the processing apparatus includes display apparatus for displaying processing results.

The present invention, therefore, provides in some, but not necessarily all, embodiments, a method for measuring a wall thickness of a wall of a tubular member, the method including positioning a device on an outer surface of the tubular member, the device as any described herein according to the present invention for measuring tubular wall thickness, sending ultrasonic signals from an ultrasonic probe apparatus of the device through the tubular member's wall, and receiving and processing the signals with receiving/processing apparatus to produce a wall thickness measurement.

In conclusion, therefore, it is seen that the present invention and the embodiments disclosed herein and those covered by the appended claims are well adapted to carry out the objectives and obtain the ends set forth. Certain changes can be made in the subject matter described, shown and claimed without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form its principles may be utilized.

What is claimed is:

1. A detector for detecting a location of a flaw on a tubular member, the tubular member having a longitudinal axis, the detector comprising
   a body,
   a dial rotatably mounted to the body, the dial with direction indications thereon for indicating position of the dial with respect to the longitudinal axis of the tubular member,
   ultrasonic probe apparatus secured to the dial for selective positioning by rotating the dial for facilitating location of a flaw of the tubular member,
   a coupling device mounted to the body beneath the ultrasonic probe apparatus, the coupling device containing coupling fluid,
   wherein the coupling device rotates with the dial,
   wherein the tubular member has an outer curved surface and the coupling device includes a flexible member for contacting the outer curved surface of the tubular member and for conforming thereto to facilitate operation of the ultrasonic probe apparatus,
   roller apparatus on the body for facilitating movement of the body over a surface of the tubular member, the roller apparatus comprising two spaced-apart pairs of spaced-apart rotatable rollers, said pairs of spaced-apart rotatable rollers for aligning the body with the longitudinal axis of the tubular member by placing the rotatable rollers in contact with the tubular member, and
   access apparatus for introducing coupling fluid into the coupling device and for evacuating coupling fluid from the coupling device.

2. The detector of claim 1 further comprising
   ultrasonic probe apparatus on the detector for measuring wall thickness of a tubular member.

3. The detector of claim 1 further comprising
   processing apparatus in communication with the ultrasonic probe apparatus for receiving and processing signals from the ultrasonic probe apparatus.

4. The detector of claim 1 wherein the processing apparatus includes display apparatus for displaying processing results.

5. A detector for detecting a location of a flaw on a tubular member, the tubular member having a longitudinal axis, the detector comprising
   a body,
   a dial rotatably mounted to the body, the dial with direction indications thereon for indicating position of the dial with respect to the longitudinal axis of the tubular member, and
   ultrasonic probe apparatus secured to the dial for selective positioning by rotating the dial for facilitating location of a flaw of the tubular member,
   a roller apparatus on the body for facilitating movement of the body over a surface of the tubular member, the roller apparatus comprising two spaced-apart pairs of spaced-apart rotatable rollers and wherein the spaced-apart rotatable rollers of each pair of spaced-apart rotatable rollers are sufficiently spaced-apart to align the body with the longitudinal axis of the tubular member when the rotatable rollers are in contact with the tubular member.

6. The detector of claim 5 further comprising
   a coupling device mounted to the body beneath the ultrasonic probe apparatus, the coupling device containing coupling fluid.

7. The detector of claim 5 wherein the coupling device rotates with the dial.

8. The detector of claim 6 wherein the tubular member has an outer curved surface and the coupling device Includes a flexible member for contacting the outer curved surface of the tubular and for conforming thereto to facilitate operation of the ultrasonic probe apparatus.

9. The detector of claim 5 wherein the direction indications correspond to an angular measurement indicating an angle with respect to the longitudinal axis of the tubular member.

10. The detector of claim 9 wherein the dial can be set to correspond to an angular measurement corresponding to an angle of a flaw with respect to the longitudinal axis of the tubular member.

11. The detector of claim 6 further comprising
    access apparatus for introducing coupling fluid into the coupling device and for evacuating coupling fluid from the coupling device.

12. The detector of claim 5 further comprising handle apparatus connected to the body for facilitating handling of the detector.

13. The detector of claim 5 further comprising
    ultrasonic probe apparatus on the detector for measuring wall thickness of a tubular member.

14. The detector of claim 5 further comprising processing apparatus in communication with the ultrasonic probe apparatus for receiving and processing signals from the ultrasonic probe apparatus.

15. The detector of claim 14 wherein the processing apparatus includes display apparatus for displaying processing results.

16. A method for detecting a location of a flaw on a tubular member having a longitudinal axis, the method comprising
    positioning a detector on an outer surface of the tubular member, the detector comprising a body, a dial rotatably mounted to the body, the dial with direction indications thereon for indicating position of the dial with respect to the longitudinal axis of the tubular member, ultrasonic probe apparatus secured to the dial for selective positioning by rotating the dial for facilitating location of a flaw of the tubular member, and a roller apparatus for facilitating movement of the body over a surface of the tubular member, the roller apparatus comprising two spaced-apart pairs of spaced-apart rotatable rollers and wherein the spaced-apart rotatable rollers of each pair of spaced-apart rotatable rollers are sufficiently spaced-apart to align the body with the longitudinal axis of the tubular member when the rotatable rollers are in contact with the tubular member, rotating the dial of the detector to selectively position the ultrasonic probe apparatus with respect to the longitudinal axis of the tubular member, and locating a flaw with the detector.

17. The method of claim 16 wherein the detector includes ultrasonic probe apparatus for measuring a wall thickness of the tubular member, the method further comprising measuring a wall thickness of the tubular member with the detector.

* * * * *